United States Patent [19]

Lachhein

[11] Patent Number: 4,831,138
[45] Date of Patent: May 16, 1989

[54] PROCESS FOR THE PREPARATION OF AMINOPYRIMIDINES

[75] Inventor: Stephen Lachhein, Hofheim am Taunus, Fed. Rep. of Germany

[73] Assignee: Hoechst Aktiengesellschaft, Frankfurt am Main, Fed. Rep. of Germany

[21] Appl. No.: 132,484

[22] Filed: Dec. 14, 1987

[30] Foreign Application Priority Data

Dec. 16, 1986 [DE] Fed. Rep. of Germany ....... 3642832

[51] Int. Cl.$^4$ .......................................... C07D 239/47
[52] U.S. Cl. ..................................... 544/320; 544/321
[58] Field of Search ................. 544/320, 321; 548/337

[56] References Cited

U.S. PATENT DOCUMENTS

| | | | |
|---|---|---|---|
| 3,985,785 | 10/1976 | Edenhofer et al. ................. | 544/326 |
| 4,032,559 | 6/1977 | McCall et al. ....................... | 544/402 |
| 4,169,179 | 9/1979 | Bussey, Jr. ............................ | 428/159 |
| 4,492,598 | 1/1985 | Willms et al. ........................... | 71/93 |

FOREIGN PATENT DOCUMENTS

| | | |
|---|---|---|
| 0024200 | 2/1981 | European Pat. Off. . |
| 0071958 | 2/1983 | European Pat. Off. . |
| 2426913 | 12/1975 | Fed. Rep. of Germany . |

OTHER PUBLICATIONS

Braker et al., J.A.C.S., vol. 69, pp. 3072-3078 (1947), "Substituted Sulfanilamidopyrimidines".
Fisher et al., J.A.C.S., vol 54, pp. 727-733 (1932), "Researches on Pyrimidines ...."
Sharanin et al., Chem. Abst. 108-204588f (1988), "Nitrile Cyclization ...."
Angew. Chem., "Neue Umsetzungen mit Cyansaeure-estern", Von Ernst Grigat, vol. 84, pp. 1008 (1972).
Angew. Chem. Int. Ed., "New Reactions with Cyanic Esters", Ernst Grigat, vol. 11, p. 949 (1972).
J. Am. Chem. Soc., "Orthoesters and Related Compounds from Malono- and Succinonitriles", S. M. McElvain and Juel P. Schroeder, vol. 71, p. 40 (1949).

*Primary Examiner*—Donald G. Daus
*Assistant Examiner*—Cecilia Shen
*Attorney, Agent, or Firm*—Curtis, Morris & Safford

[57] ABSTRACT

Process for the preparation of aminopyrimidines
Pyrimidines of the formula I

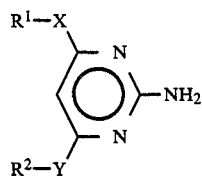

in which X and Y denote oxygen or sulfur and $R^1$ and $R^2$ denote $C_1$-$C_4$-alkyl, ($C_1$-$C_4$-alkoxy)-$C_1$-$C_2$-alkyl or halo-$C_1$-$C_4$-alkyl, are obtained through reaction of propanediimidates of the formula II

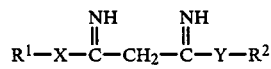

or salts thereof with cyanurates of the formula $R^3$—O—CN in which $R^3$ denotes $C_1$-$C_4$-alkyl, phenyl, phenyl which is substituted by 1, 2 or 3 radicals from the series comprising halogen, $C_1$-$C_4$-alkoxy and $C_1$-$C_4$-alkyl radicals, α- or β-naphthyl or halo-$C_1$-$C_4$-alkyl, in an organic solvent which is inert under the reaction conditions. The one-step process permits efficient preparation of the compounds of the formula I, which can be used as intermediates for the preparation of herbicidal sulfonylureas.

10 Claims, No Drawings

PROCESS FOR THE PREPARATION OF AMINOPYRIMIDINES

DESCRIPTION

The invention relates to a process for the preparation of pyrimidines of the formula I

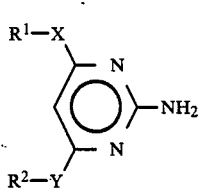

in which
X and Y, independently of one another, denote oxygen or sulfur, and
$R^1$ and $R^2$, independently of one another, denote $(C_1-C_4)$-alkyl, $(C_1-C_4)$alkoxy-$(C_1-C_2)$alkyl or halo$(C_1-C_4)$alkyl, wherein a propanediimidate of the formula II

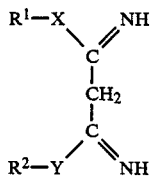

in which $R^1$ and $R^2$ are as defined in formula I, or one of its salts, is reacted with a cyanurate of the formula III $$R^3-O-C\equiv N \qquad III$$

in which $R^3$ denotes $(C_1-C_4)$alkyl, phenyl, phenyl which is substituted by 1, 2 or 3 radicals from the series comprising the halogen, $(C_1-C_4)$alkoxy and $(C_1-C_4)$alkyl radicals, α- or β-naphthyl or halo$(C_1-C_4)$alkyl, in an inert organic solvent.

Compounds of the formula I are valuable intermediates in the preparation of sulfonylureas having a herbicidal action; see, for example, U.S. Pat. No. 4,169,719 or EP-A-071,958 (U.S. Pat. No. 4,492,598).

The reaction of nucleophiles and dinucleophiles with cyanurates is known (E. Grigat, Angew. Chem. 84, 1008 (1972); Angew. Chem. Int. Ed. Vol 11, 949 (1972)).

It is furthermore known that pyrimidines of the formula I can be prepared by reacting propanediimidates with aqueous cyanamide solution or cyanogen chloride in a two-step or three-step process (EP-A-0,024,200), the formation and subsequent isolation of an N-cyanoimidate as an intermediate being regarded as characteristic process features. However, the final product yields obtained in this process are unsatisfactory. Further disadvantages of the process mentioned are: the formation of not inconsiderable amounts of byproducts, the necessity for carrying out the reaction in a narrow pH range, and the additional use of a base. In addition, it is disadvantageous that the inorganic salts formed during the reaction, specifically when aqueous cyanamide solution is used, are discharged in dissolved form into the waste water, from which they must be removed by additional measures.

Surprisingly, the process according to the invention proceeds, in contrast, in a technically simple one-step process without intermediates which can be isolated, permitting the reaction to be carried out without pH control. Byproducts are formed only to a minor extent.

In the process according to the invention, the imide nitrogen attacks the cyanurate without a cyanoimidate being passed through or formed as an intermediate. The high selectivity during the formation of compounds of the formula I, and the high yields associated with this, were unexpected.

In the course of the reaction, no salts are formed which could lead to waste water pollution. Besides the technical and economic advantages described above, this aspect should be regarded as an advance from an ecological point of view. When the reaction is complete, extraction of the alcohol ($R^3OH$) formed and removal of the solvent, which is recovered virtually quantitatively, by distillation leaves the final product in high purity.

The process according to the invention is expediently carried out by isolating the propanediimidate as the monosalt or disalt or as the bisimidate, and reacting it in solution or as a suspension with the cyanurate of the formula III at reaction temperatures of 0°–180° C., preferably 20°–140° C. Preferred salts of the propanediimidate are those of hydrofluoric acid, hydrochloric acid or hydrobromic acid or of sulfuric acid or phosphoric acid. Haloalkyl radicals $R^1$, $R^2$ and $R^3$ are, for example, $CH_2Cl$, $CHCl_2$, $CCl_3$, $CH_2CH_2Cl$ or $CH_2CF_3$. X and Y preferably denote oxygen. $R^1$ and $R^2$ preferably denote $(C_1-C_4)$-alkyl, in particular methyl. $R^3$ preferably denotes phenyl which may have up to 3 substituents, in particular 1 or 2 substituents, from the series comprising the chlorine, methyl and methoxy radicals, or β-naphthyl.

Suitable inert organic solvents are those which are inert under the particular reaction conditions. For example, the inert organic solvents used can be alcohols, such as methanol, ethanol and propanol, ketones, such as acetone and methyl isobutyl ketone, ethers, such as diethyl ether, dioxane and tetrahydrofuran, esters, such as methyl acetate, ethyl acetate and butyl acetate, hydrocarbons, such as toluene, xylene, hexane and cyclohexane, nitriles, such as acetonitrile, and halogenated hydrocarbons, such as chloroform and methylene chloride, or mixtures of the solvents mentioned.

In order to prevent the interfering influence of oxygen on the reaction, it is expedient to work under an inert gas atmosphere, for example under nitrogen.

The compounds of the formula II can be prepared by known methods (S. M. McElvain and I. D. Schroeder, JACS 71, 40 (1949); B. Harstun, German Offenlegungsschrift No. 2,426,913).

The monosalt and the bisimidate of these compounds can be prepared from the corresponding disalt by reaction with bases such as alkali metal hydroxides, carbonates, hydrogen carbonates or alcoholates and alkaline earth metal hydroxides, carbonates, hydrogen carbonates, or alcoholates, in an inert solvent.

The following examples are intended to illustrate the process according to the invention in greater detail:

EXAMPLE 1

52 g of dimethylpropanediimidate and 49 g of phenyl cyanate are added to 800 ml of diethyl ether at room temperature under a blanket of nitrogen. After the mixture has been warmed at 36° C. for 5 hours, the phenol is washed out using a 10% strength sodium hydroxide solution and the solvent is removed by distillation. 55 g of product remain, corresponding to a yield of 89% of theory. The melting point is 93°–94° C.

EXAMPLE 2

49 g of phenyl cyanate and 52 g of dimethylpropanediimidate are added to 800 ml of methyl isobutyl ketone at 50° C. under a blanket of nitrogen, and the reactants are allowed to react for 5 hours. The phenol produced is extracted using sodium hydroxide solution and the solvent is removed by distillation. 56.4 g of product remain, corresponding to a yield of 91% of theory. The melting point is 92°–94° C.

EXAMPLE 3

52 g of dimethylpropanediimidate and 75.2 g of 2,4-dichlorophenyl cyanate are added to a solution of 500 ml of acetone at 40° C. under a blanket of nitrogen, and the reactants are allowed to react at 40° C. for 5 hours. After extraction of 2,4-dichlorophenol, the solvent is removed by distillation. 54.5 g of product remain, corresponding to a yield of 88% of theory. The melting point is 92°–94° C.

EXAMPLE 4

59 g of 2,4-dimethylphenyl cyanate and 67 g of dimethylpropanediimidate monohydrochloride are added to 500 ml of methyl acetate, and the reactants are allowed to react at 50° C. for 5 hours. After extraction of 2,4-dimethylphenol using sodium hydroxide solution, the solvent is removed by distillation. 53 g of product remain, corresponding to a yield of 86% of theory. The melting point is 92°–93° C.

EXAMPLE 5

52 g of dimethylpropanediimidate and 63 g of β-naphthyl cyanate are added to 500 ml of toluene at 70° C., and the reactants are allowed to react at 70° C. for 5 hours. After removal of the β-naphthol, the solvent is removed by distillation. 55.8 g of product remain, corresponding to a yield of 90% of theory.

EXAMPLE 6

52 g of dimethylpropanediimidate and 67,0 g of 2-methyl-4-chlorophenyl cyanate are added to 800 ml of toluene at 110° C. under a blanket of nitrogen, and the reactants are allowed to react at 110° C. for 5 hours. After extraction of 2-methyl-4-chlorophenol, the solvent is removed by distillation. 55.2 g of product remain, corresponding to a yield of 89.2% of theory. The melting point of the product is 92°–94° C.

EXAMPLE 7

52 g of dimethylpropanediimidate and 73,4 g of 4-chloro-2-methoxyphenyl cyanate are added to 800 ml of toluene at 90° C. under a blanket of nitrogen, and the reactants are allowed to react at 90° C. for 6 hours. After extraction of 4-chloro-2-methoxyphenol, the solvent is removed by distillation. 53.2 g of product (yield 86% of theory) having a melting point of 92°–93° C. remain.

EXAMPLES 8–19

The following compounds of the formula I can be prepared, for example, analogously to the procedures described in Examples 1–7.

| Example | X | Y | R$^1$ | R$^2$ |
|---|---|---|---|---|
| 8 | O | O | C$_2$H$_5$ | C$_2$H$_5$ |
| 9 | S | S | C$_2$H$_5$ | C$_2$H$_5$ |
| 10 | S | S | CH$_3$ | CH$_3$ |
| 11 | O | O | CH(CH$_3$)—CH$_3$ | CH(CH$_3$)—CH$_3$ |
| 12 | O | O | CF$_3$ | CF$_3$ |
| 13 | O | S | CH$_2$Cl | CH$_2$Cl |
| 14 | S | S | CH$_2$OCH$_3$ | CH$_2$OCH$_3$ |
| 15 | O | O | CH$_2$Cl | CH$_2$Cl |
| 16 | S | O | CHCl$_2$ | CHCl$_2$ |
| 17 | O | O | CH$_2$OC$_2$H$_5$ | CH$_2$OC$_2$H$_5$ |
| 18 | O | S | CH$_2$OC$_2$H$_5$ | CH$_2$OC$_2$H$_5$ |
| 19 | S | S | CF$_3$ | CF$_3$ |

I claim:

1. A process for the preparation of a compound of the formula I

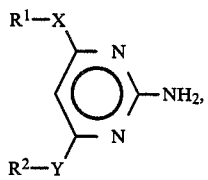

in which
X and Y, independently of one another, are oxygen or sulfur, and
R$^1$ and R$^2$, independently of one another, are (C$_1$–C$_4$)-alkyl, (C$_1$–C$_4$)alkoxy-(C$_1$–C$_4$)alkyl or halo(C$_1$–C$_4$)alkyl, wherein a propanediimidate of the formula II

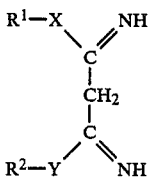

in which R$^1$ and R$^2$ are as defined in formula I, or one of its salts, is reacted with a cyanurate of the formula III

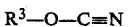

in which
R$^3$ is (C$_1$–C$_4$)alkyl, phenyl, phenyl which is substituted by 1, 2 or 3 radicals from the series consisting of the halogen, (C$_1$–C$_4$)alkoxy or (C$_1$–C$_4$)alkyl radicals, α- or β-naphthyl or halo(C$_1$–C$_4$)alkyl, in an inert organic solvent.

2. The process as claimed in claim 1, wherein, in formula I, X and Y in each case are oxygen and R$^1$ and R$^2$ in each case are (C$_1$–C$_4$)alkyl.

3. The process as claimed in claim 1, wherein the inert organic solvent used is an alcohol, a ketone, an ether, an ester, a hydrocarbon, a halogenated hydrocarbon, a nitrile or a mixture of at least two of the above-mentioned solvents.

4. The process as claimed in claim 1, wherein the solvent used is diethyl ether, acetone, methyl isobutyl ketone, methyl acetate, toluene or a mixture of at least two of these solvents.

5. The process as claimed in claim 1, wherein the salts of the compound of the formula II used are those of hydrofluoric acid, hydrochloric acid or hydrobromic acid, or of sulfuric acid or phosphoric acid.

6. The process as claimed in claim 1, wherein the reaction temperature is 0°–180° C.

7. The process as claimed in claim 1, wherein the reaction temperature is 20°–140° C.

8. The process as claimed in claim 1, wherein the reaction is carried out under an inert gas atmosphere.

9. The process as claimed in claim 1, wherein X and Y are oxygen, and $R^1$ and $R^2$ are ($C_1$–$C_4$)-alkyl, and the reaction temperaure is 0°–180° C.

10. The process as claimed in claim 1, wherein X and Y are oxygen, and $R^1$ and $R^2$ are ($C_1$–$C_4$)-alkyl, and the solvent used is an alcohol, a ketone, an ether, an ester, a hydrocarbon, a halogenated hydrocarbon, a nitrile or a mixture thereof, and the temperature is 0°–180° C.

* * * * *